US00PP16146P2

(12) United States Plant Patent
Smith

(10) Patent No.: US PP16,146 P2
(45) Date of Patent: Dec. 6, 2005

(54) ***CHRYSANTHEMUM* PLANT NAMED 'WARM YOURSULA'**

(50) Latin Name: *Chrysanthemum×morifolium*
Varietal Denomination: Warm Yoursula

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 45 days.

(21) Appl. No.: 10/937,849

(22) Filed: Sep. 8, 2004

(51) Int. Cl.[7] ..... A01H 5/00
(52) U.S. Cl. ..... Plt./290
(58) Field of Search ..... Plt./290

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Warm Yoursula', characterized by its upright, outwardly spreading and rounded plant habit; freely branching habit; freely flowering habit; decorative-type inflorescences with elongated oblong-shaped ray florets; light orange-colored ray florets; natural season flowering in mid-September in the Northern Hemisphere; and good garden performance.

2 Drawing Sheets

Botanical classification/cultivar designation: *Chrysanthemum×morifolium* cultivar Warm Yoursula.

BACKGROUND OF THE INVENTION

The present invention relates to a new and distict cultivar of *Chrysanthemum* plant, botanically known as *Chrysanthemum×morifolium,* commercially known as a garden-type *Chrysanthemum* and hereinafter referred to by the name 'Warm Yoursula'.

The new *Chrysanthemum* is a naturally-occurring whole plant mutation of the *Chrysanthemum×morifolium* cultivar Yoursula, disclosed in U.S. Plant Pat. No. 13,641. The new *Chrysanthemum* was discovered and selected by the Inventor as a single flowering plant within a population of plants of the cultivar Yoursula in a controlled environment in Alva, Fla. in April, 2002. The selection of this plant was based on its desirable inflorescence form, attractive floret coloration and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Warm Yoursula has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Warm Yoursula'. These characteristics in combination distinguish 'Warm Yoursula' as a new and distinct cultivar of *Chrysanthemum:*

1. Upright, outwardly spreading and rounded plant habit.
2. Freely branching habit.
3. Freely flowering habit.
4. Decorative-type inflorescences with elongated oblong-shaped ray florets.

5. Light orange-colored ray florets.
6. Natural season flowering in mid-September in the Northern Hemisphere.
7. Good garden performance.

In side-by-side comparisons conducted in Alva, Fla. under natural season conditions, plants of the new *Chrysanthemum* differed from plants of the parent, the cultivar Yoursula, in the following characteristics:

1. Plants of the new *Chrysanthemum* flowered about two or three days later than plants of the cultivar Yoursula.
2. Plants of the new *Chrysanthemum* and the cultivar Yoursula differed in ray floret coloration as plants of the cultivar Yoursula had light purple-colored ray florets.

Plants of the new *Chrysanthemum* can be compared to plants of the *Chrysanthemum* cultivar Yogretchen, disclosed in U.S. Plant Pat. No. 13,672. In side-by-side comparisons conducted in Alva, Fla. under natural season conditions, plants of the new *Chrysanthemum* differed from plants of the cultivar Yogretchen in the following characteristics:

1. Plants of the new *Chrysanthemum* were slightly smaller and more rounded than plants of the cultivar Yogretchen.
2. Inflorescences of plants of the new *Chrysanthemum* had more disc florets than inflorescences of plants of the cultivar Yogretchen.
3. Plants of the new *Chrysanthemum* and the cultivar Yogretchen differed in ray floret coloration as plants of the cultivar Yogretchen had darker orange-colored ray florets.
4. Plants of the new *Chrysanthemum* flowered three days later than plants of the cultivar Yogretchen.

Plants of the new *Chrysanthemum* can also be compared to plants of the *Chrysanthemum* cultivar Gedi Two Omol, disclosed in U.S. Plant Pat. No. 14,382. In side-by-side comparisons conducted in Alva, Fla. under natural season conditions, plants of the new *Chrysanthemum* differed from plants of the cultivar Gedi Two Omol in the following characteristics:

1. Plants of the new *Chrysanthemum* were shorter and more rounded than plants of the cultivar Gedi Two Omol.

2. Plants of the new *Chrysanthemum* flowered more uniformly than plants of the cultivar Gedi Two Omol.
3. Inflorescences of plants of the new *Chrysanthemum* had more disc florets than inflorescences of plants of the cultivar Gedi Two Omol.
4. Ray florets of plants of the new *Chrysanthemum* resisted fading better than ray florets of plants of the cultivar Gedi Two Omol.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering plant of 'Warm Yoursula' grown in a container.

The photograph on the second sheet comprises a close-up view of typical inflorescences of the cultivar 'Warm Yoursula'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Warm Yoursula.

Commercial classification: Decorative-type garden *Chrysanthemum.*

Parentage: Naturally-occuring whole plant mutation of the *Chrysanthemum×morifolium* cultivar Yoursula, disclosed in U.S. Plant Pat. No. 13,641.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum.* Inverted triangle with rounded crown. Stems initially upright, then outwardly spreading. Freely branching with about 14 lateral branches per plant. Moderately vigorous.

*Plant height.*—About 14 cm.

*Plant diameter.*—About 20 cm.

*Lateral branches.*—Length: About 12.5 cm. Diameter: About 4 mm. Internode length: About 1.3 cm. Strength: Strong. Texture: Pubescent. Color: Close to 146A.

*Foliage description.*—Leaf arrangement: Alternate. Length: About 2.8 cm. Width: About 2.7 cm. Apex: Mucronate. Base: Attenuate to truncate. Margin: Palmately and deeply lobed; sinuses mostly divergent. Texture, upper and lower surfaces: Pubescent. Color: Developing foliage, upper surface: More green than 147A. Developing foliage, lower surface: Close to 146A. Fully expanded foliage, upper surface: More green than 147A. Fully expanded foliage, lower surface: More green than 147B. Venation, upper suface: Close to 147A. Venation, lower surface: Close to 146A. Petiole: Length: About 1.7 cm. Diameter: About 2.5 mm. Texture, upper and lower surfaces: Pubescent. Color, upper and lower surfaces: Close to 146A.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherical in shape. Freely flowering habit; about eight inflorescences develop per lateral branch. Inflorescences persistent. Inflorescences not fragrant.

*Flowering response.*—Under natural season conditions, plants flower in mid-September in the Northern Hemisphere.

*Inflorescence bud (before showing color).*—Height: About 7 mm. Diameter: About 8 mm. Shape: Oblate. Color (lower surface of phyllaries): More green than 147A.

*Inflorescence size.*—Diameter: About 3.5 cm. Depth (height): About 1.5 cm. Disc diameter: About 3 mm. Receptacle diameter: About 4 mm. Receptacle height: About 6 mm.

*Ray florets.*—Shape: Elongated oblong. Length: About 1.7 cm. Corolla tube length: About 3.5 mm. Width: About 5 mm. Apex: Emarginate. Margin: Fused. Texture: Smooth, glabrous; satiny. Surface: Concave. Orientation: Initially upright, then perpendicular to the peduncle. Number of ray florets per inflorescence: About 190 in numerous whorls. Color: When opening, upper and lower surfaces: Close to 6A faintly overlain with 46A. Fully opened, upper surface: 10A less faintly overlain with close to 45A to 46A. Fully opened, lower surface: 10A to 10C.

*Disc florets.*—Shape: Tubular; apex dentate, five-pointed. Length: About 4 mm. Width, apex: About 1.5 mm. Width, base: About 1 mm. Number of disc florets per inflorescence: Very few, less than 15; inconspicuous. Color: Immature: Close to 154A. Mature: Apex: Close to 9A. Mid-section: Close to 154D. Base: Close to 155D.

*Phyllaries.*—Quantity per inflorescence: About 18. Length: About 7 mm. Width: About 4 mm. Shape: Deltoid, elongated. Apex: Acute. Base: Truncate, fused. Margin: Entire. Texture, upper surface: Smooth, waxy. Texture, lower surface: Pubescent.

Color, upper surface: More green than 146A. Color, lower surface: More green than 147A.

*Peduncle.*—Length: First peduncle: About 4.1 cm. Fourth peduncle: About 7.2 cm. Seventh peduncle: About 8.4 cm. Diameter: About 2.5 mm. Strength: Strong. Aspect: About 35 to 40° from vertical. Texture: Pubescent. Color: Close to 146A.

*Reproductive organs.*—Androecium: Present on disc florets only. Anther color: Close to 12A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have not been observed to be have good garden performance and to be tolerant to rain, wind and temperatures ranging from 0 to greater than 38° C.

It is claimed:

1. A new and distinct cultivar of *Chrysanthemum* plant named 'Warm Yoursula', as illustrated and described.

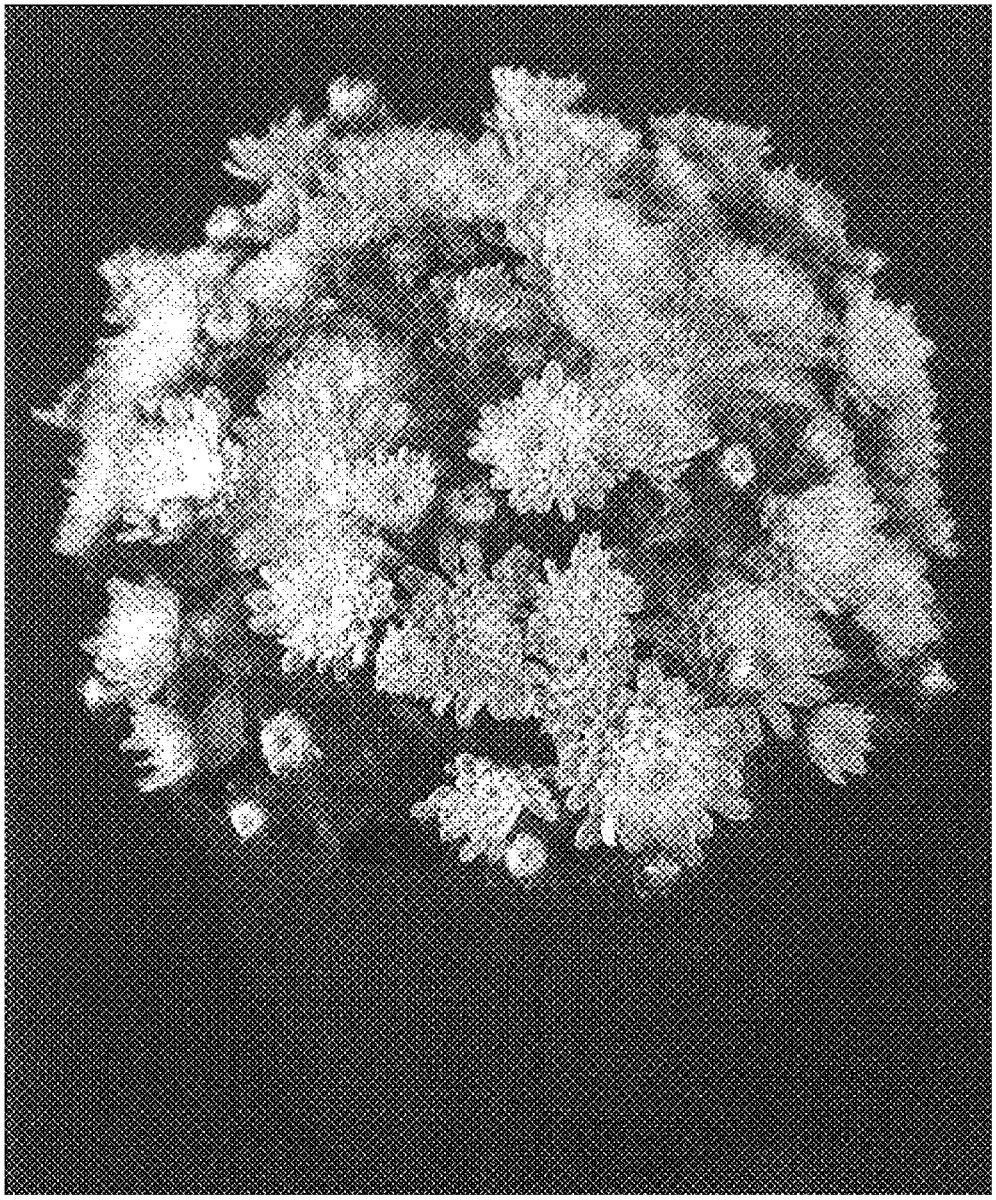

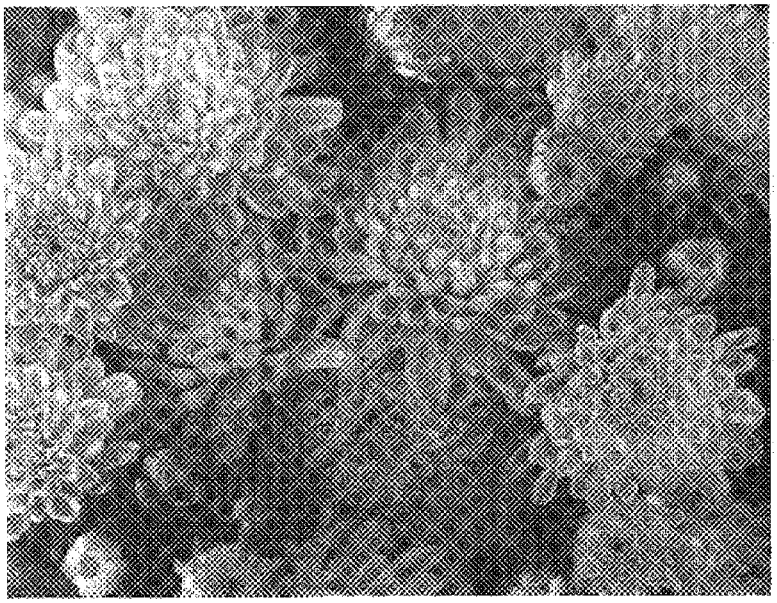

* * * * *